United States Patent
Yamamoto et al.

(10) Patent No.: US 9,797,886 B2
(45) Date of Patent: Oct. 24, 2017

(54) AGGLUTINATION ENHANCER

(75) Inventors: Naoyuki Yamamoto, Amagasaki (JP); Tsutomu Masuda, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 497 days.

(21) Appl. No.: 14/123,899

(22) PCT Filed: Jun. 4, 2012

(86) PCT No.: PCT/JP2012/064355
§ 371 (c)(1),
(2), (4) Date: Dec. 4, 2013

(87) PCT Pub. No.: WO2012/169453
PCT Pub. Date: Dec. 13, 2012

(65) Prior Publication Data
US 2014/0113311 A1    Apr. 24, 2014

(30) Foreign Application Priority Data
Jun. 7, 2011 (JP) .................. 2011-127076

(51) Int. Cl.
*G01N 33/53* (2006.01)
*C08F 220/36* (2006.01)
*C08F 220/60* (2006.01)
*G01N 33/542* (2006.01)

(52) U.S. Cl.
CPC ....... *G01N 33/5306* (2013.01); *C08F 220/36* (2013.01); *C08F 220/60* (2013.01); *G01N 33/542* (2013.01)

(58) Field of Classification Search
CPC . C08F 220/36; C08F 220/60; G01N 33/5306; G01N 33/542
See application file for complete search history.

(56) References Cited

U.S. PATENT DOCUMENTS

| | | | |
|---|---|---|---|
| 2003/0166302 A1 | 9/2003 | Shigenobu et al. | |
| 2004/0157276 A1* | 8/2004 | Sumida .................. | C08F 30/02 435/7.23 |

FOREIGN PATENT DOCUMENTS

| | | |
|---|---|---|
| JP | 58-047256 A | 3/1983 |
| JP | 04-122858 A | 4/1992 |
| JP | 2002-365296 A | 12/2002 |
| JP | 2007-225343 A | 9/2007 |
| WO | WO 02/18953 A1 | 3/2002 |

OTHER PUBLICATIONS

The Supplementary European Search Report and Opinion issued for the European counterpart of the instant application, EP 2720041, European application No. EP 12796593 on Dec. 1, 2014.*
Kudaibergenov et al., " Polymeric Betaines: Synthesis, Characterization, and Application," Adv. Polym. Sci., 2006, vol. 201, pp. 157-224.*
Japanese Patent Office, International Search Report in International Patent Application No. PCT/JP2012/064355 (Sep. 11, 2012).

* cited by examiner

*Primary Examiner* — Galina Yakovleva
(74) *Attorney, Agent, or Firm* — Leydig, Voit & Mayer, Ltd.

(57) ABSTRACT

The purpose of the present invention is to provide an agglutination enhancer which shows superior agglutination enhancing effect to those of conventional immunoagglutination enhancers, and the present invention relates to an agglutination enhancer for an immunoagglutination measurement method which comprises a polymer having a monomer unit shown by the following general formula [1]:

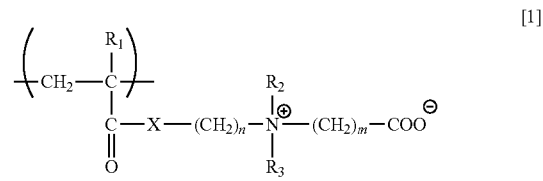

[1]

(Wherein $R_1$ represents a hydrogen atom or a methyl group; $R_2$ and $R_3$ independently represent a methyl group or an ethyl group, respectively; X represents —NH— or an oxygen atom; n represents an integer of 1 to 6; and m represents an integer of 1 to 3), and an immunoagglutination measurement method in which, in the coexistence of the above-described agglutination enhancer for immunoagglutination measurement method, an antibody against analyte or an antigen for the analyte is brought into contact with the analyte to cause an antigen-antibody reaction.

5 Claims, No Drawings

AGGLUTINATION ENHANCER

CROSS-REFERENCE TO RELATED APPLICATIONS

This patent application is the U.S. national phase of International Patent Application No. PCT/JP2012/064355 filed Jun. 4, 2012, which claims the benefit of Japanese Patent Application No. 2011-127076, filed on Jun. 7, 2011, which are incorporated by reference in their entireties herein.

TECHNICAL FIELD

The present invention relates to an agglutination enhancer for use in an immunoagglutination measurement method, and the immunoagglutination measurement method using the agglutination enhancer.

BACKGROUND ART

For example, it has been carried out conventionally as an immunoagglutination measurement method that the presence of an analyte is confirmed or the concentration of an analyte is measured from the degree of the agglutination generated with the use of an insoluble carrier such as a latex immobilized an antigen or an antibody reacting with the analyte, in order to determine the presence or the concentration of the analyte in a biological sample such as serum, plasma, and urine.

In this immunoagglutination method, an immunoagglutination enhancer which facilitate the generation of agglutination based on an antigen-antibody reaction is usually employed for the purpose of improving the sensitivity. As said immunoagglutination enhancer, polyethylene glycol (PEG) and the like have been known well, however, the PEG has a problem such that the PEG salts out in a solution with high salt concentration, causing a blank value increased, and therefore accuracy of determination becomes worse.

And so, the use of a polymer containing methacryloyloxyethyl phosphorylcholine (MPC) as an immunoagglutination enhancer which solves such problem has been devised (Patent Literature 1).

CITATION LIST

Patent Literature

Patent Literature 1: JP A-2002-365296.

SUMMARY OF INVENTION

Technical Problem

Currently, an immunoagglutination measurement method which enables to perform measurement with much higher sensitivity has been required, and development of an immunoagglutination enhancer which shows a superior agglutination enhancing effect to those of said MPC-containing polymers has been desired. In view of above-described situation, the present invention is to provide an agglutination enhancer which enables high sensitive immunoagglutination measurement, and which shows a superior agglutination enhancing effect to those of the conventional immunoagglutination enhancers.

Solution to Problem

The present inventors have extensively studied to solve the above-described problems, and as a result, have found that a polymer having monomer units shown by the following general formula [1]

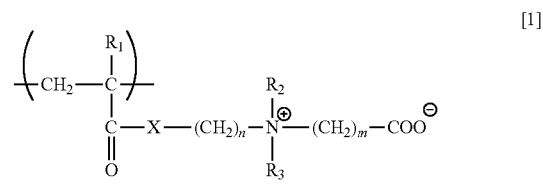

(Wherein $R_1$ represents a hydrogen atom or a methyl group, $R_2$ and $R_3$ represent independently a methyl group or an ethyl group, respectively, X represents —NH— or an oxygen atom, n represents an integer of 1 to 6, and m represents an integer of 1 to 3) shows superior agglutination enhancing effect to those of conventional immunoagglutination enhancers, and have thus completed the present invention.

That is, the present invention relates to "an agglutination enhancer for immunoagglutination measurement method comprising a polymer having a monomer unit shown by the following general formula [1]

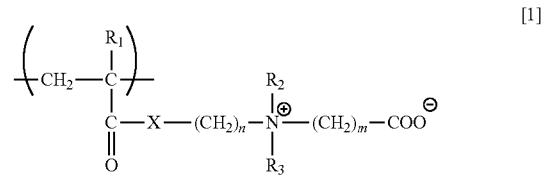

(Wherein $R_1$, $R_2$, $R_3$, X, n and m are the same as described above.), a reagent for immunoagglutination measurement method comprising an agglutination enhancer in which the above-described polymer is a copolymer having a monomer unit shown by the above-described general formula [1] and a monomer unit shown by the following general formula [2]

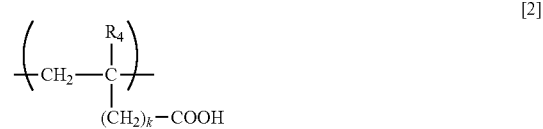

(Wherein $R_4$ represents a hydrogen atom or a methyl group, and k represents an integer of 1 to 10) and an immunoagglutination measurement method which comprises that in the coexistence of the above-described agglutination enhancer for immunoagglutination measurement method, an antibody against the analyte or an antigen for the analyte is brought into contact with the analyte to cause an antigen-antibody reaction."

Advantageous Effects of Invention

The immunoagglutination enhancer of the present invention has a greater agglutination enhancing effect as compared with the conventional immunoagglutination enhancers. Therefore, generation of agglutination by an antigen-antibody reaction is made easy by employing immunoagglutination enhancer of the present invention, in the immunoagglutination measurement method such as turbidimetric immunoassay and nephelometric immunoassay which utilize the agglutination of antigen-antibody reaction product produced with the use of a carrier such as latex particles to which antigen or antibody has been immobilized. As a result, the immunoagglutination enhancer of the present invention enables a highly sensitive measurement.

DESCRIPTION OF EMBODIMENTS

The polymer to be used in the agglutination enhancer for immunoagglutination measurement method of the present invention (hereinafter, sometimes may be written briefly as an agglutination enhancer of the present invention) may be either homopolymer or copolymer as long as it has a monomer unit shown by the general formula [1]. Specifically, said copolymer includes, for example, the one which consists of a monomer unit shown by the general formula [1] and a monomer unit shown by the general formula [2].

The weight-average molecular weight of the polymer to be employed in the agglutination enhancer of the present invention is usually 50,000 to 3,000,000, preferably 100,000 to 3,000,000, and more preferably 200,000 to 3,000,000. In addition, in the case where said agglutination enhancer is a copolymer, its weight-average molecular weight is usually 50,000 to 3,000,000, preferably 100,000 to 3,000,000, and more preferably 200,000 to 3,000,000.

(1) A Homopolymer which has a Monomer Unit Shown by the General Formula [1]

$R_1$ in the general formula [1] includes a hydrogen atom, a methyl group and the like, and a methyl groups is preferable.

$R_2$ in the general formula [1] includes a methyl group, an ethyl group and the like, and a methyl groups is preferable.

$R_3$ in the general formula [1] includes a methyl group, an ethyl group and the like, and a methyl groups is preferable.

X in the general formula [1] represents —NH— or an oxygen atom, and an oxygen atom is preferable.

"n" in the general formula [1] represents an integer of usually 1 to 6, and an integer of 2 to 4 is preferable, and an integer of 2 to 3 is more preferable.

"m" in the general formula [1] represents an integer of usually 1 to 3, and an integer of 1 to 2 is preferable, and 1 is more preferable.

A specific preferable example of the monomer unit shown by the general formula [1] includes, for example, the following general formula [1-1] to [1-8].

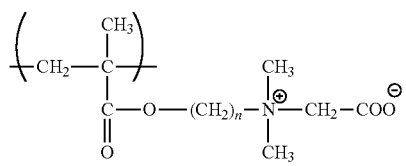

[1-1]

(Wherein n represents an integer of 1 to 6)

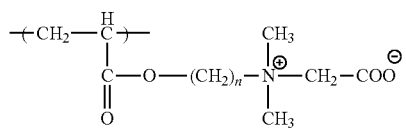

[1-2]

(Wherein n represents an integer of 1 to 6)

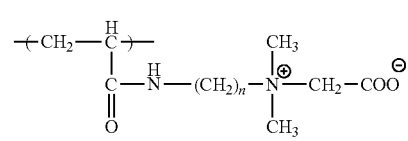

[1-3]

(Wherein n represents an integer of 1 to 6)

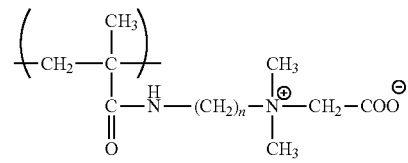

[1-4]

(Wherein n represents an integer of 1 to 6)

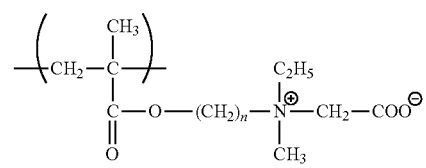

[1-5]

(Wherein n represents an integer of 1 to 6)

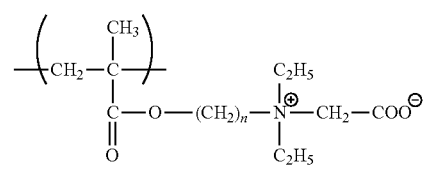

[1-6]

(Wherein n represents an integer of 1 to 6)

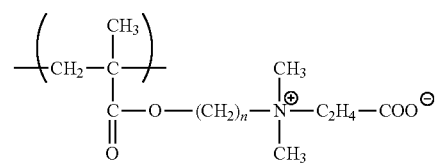

[1-7]

(Wherein n represents an integer of 1 to 6)

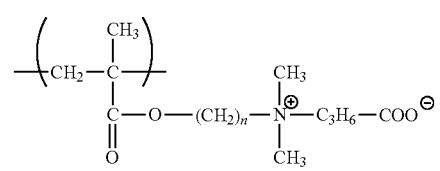

[1-8]

(Wherein n represents an integer of 1 to 6)

Among them, the general formulae [1-1] to [1-4] are preferable, the general formula [1-1], the general formula [1-3], and the general formula [1-4] are more preferable, and the general formula [1-1] is particularly preferable. More specifically, the ones which are shown by the following [1-1-1], [1-1-2], [1-3-1], and [1-4-1] are preferable:

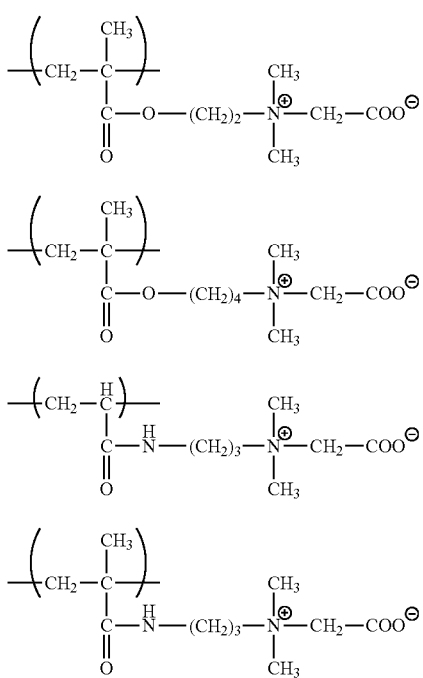

(2) Method for Production of a Homopolymer which has Monomer Unit Shown by The General Formula [1]

The homopolymer which has monomer unit shown by the general formula [1] can be produced by reacting, for example, a (meth) acrylic acid derivative shown by the following general formula [3]

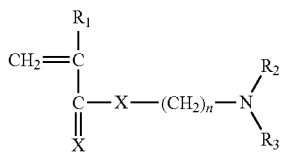

(Wherein $R_1$, $R_2$, $R_3$, X, and n are the same as described above) with, for example, a carboxylic acids compound shown by the following general formula [4],

X—(CH$_2$)$_m$—COOH  [4]

(Wherein X represents a halogen atom, and m is the same as described above.) in an appropriate solvent, and the obtained monomer is further polymerized by polymerization reaction well known per se.

A specific example of the (meth) acrylic acid derivative shown by the general formula [3] includes, for example, N-[2-(dimethylamino) ethyl]methacrylate, N-[3-(dimethylamino) propyl]methacrylate, N-[4-(dimethylamino) butyl] methacrylate, N-[5-(dimethylamino) pentyl]methacrylate, N-[6-(dimethylamino) hexyl]methacrylate; N-[2-(dimethylamino) ethyl]acrylate, N-[3-(dimethylamino) propyl]acrylate, N-[4-(dimethylamino) butyl]acrylate, N-[5-(dimethylamino) pentyl]acrylate, N-[6-(dimethylamino) hexyl] acrylate; N-[2-(dimethylamino) ethyl]acrylamide, N-[3-(dimethylamino) propyl]acrylamide, N-[4-(dimethylamino) butyl]acrylamide, N-[5-(dimethylamino) pentyl]acrylamide, N-[6-(dimethylamino) hexyl]acrylamide; N-[2-(dimethylamino) ethyl]methacrylamide, N-[3-(dimethylamino) propyl]methacrylamide, N-[4-(dimethylamino) butyl]methacrylamide, N-[5-(dimethylamino) pentyl]methacrylamide, N-[6-(dimethylamino) hexyl]methacrylamide; N-[2-(ethylmethylamino) ethyl]methacrylate, N-[3-(ethylmethylamino) propyl]methacrylate, N-[4-(ethylmethylamino) butyl]methacrylate, N-[5-(ethylmethylamino) pentyl]methacrylate, N-[6-(ethylmethylamino) hexyl]methacrylate; N-[2-(diethylamino) ethyl]methacrylate, N-[3-(diethylamino) propyl]methacrylate, N-[4-(diethylamino) butyl]methacrylate, N-[5-(diethylamino) pentyl]methacrylate, N-[6-(diethylamino) hexyl]methacrylate, etc., and N-[2-(dimethylamino) ethyl]methacrylate, N-[4-(dimethylamino) butyl]methacrylate, N-[3-(dimethylamino) propyl]acrylamide, N-[3-(dimethylamino) propyl]methacrylamide, N-[2-(diethylamino) ethyl]methacrylate, N-[3-(diethylamino) propyl]methacrylate, N-[4-(diethylamino) butyl]methacrylate, N-[3-(diethylamino) propyl]acrylamide, etc. are preferable. Among them, N-[2-(dimethylamino) ethyl]methacrylate, N-[4-(dimethylamino) butyl]methacrylate, N-[3-(dimethylamino) propyl] acrylamide, N-[3-(dimethylamino) propyl]methacrylamide, etc. are particularly preferable. It should be noted that, for these (meth) acrylic acid derivatives, commercially available products or the one synthesized appropriately from (meth) acrylic acid by a conventional method may be employed.

A halogen atom represented by X in the general formula [4] includes, for example, fluorine, chlorine, bromine, iodine etc., and, chlorine and bromine are particularly preferable.

A specific example of carboxylic acid compound shown by the general formula [4] includes, for example, chloroacetic acid, fluoroacetic acid, bromoacetic acid, iodoacetic acid, chloropropionic acid, fluoropropionic acid, bromopropionic acid, iodopropionic acid, chlorobutanoic acid, fluorobutanoic acid, bromobutanoic acid, iodobutanoic acid etc., and, bromoacetic acid, chloropropionic acid, and chloroacetic acid are preferable, and chloroacetic acid is particularly preferable among them.

The usage of carboxylic acid compound shown by the general formula [4] may be usually 0.5 to 3 times mole, preferably 1 to 2 times mole of the (meth) acrylic acid derivative shown by the general formula [3].

A reaction solvent to be used at the time of a reaction of the (meth) acrylic acid derivative shown by the above-described general formula [3] with the carboxylic acid compound shown by the general formula [4] or the salt thereof includes, for example, hydrocarbons such as toluene, xylene, benzene, cyclohexane, n-hexane, and n-octane, for example, alcohols such as methanol, ethanol, n-propanol, isopropanol, n-butanol, isobutanol, and tert-butanol, dimethylformamide (DMF) and water etc., and, the alcohols are preferable, and among them, methanol, ethanol, n-propanol and isopropanol are preferable. In addition, the above-described solvent may be used by mixing two or more kinds appropriately. The amount of reaction solvent to be used is usually 100 to 300 mL for 50 g of the total amount of (meth) acrylic acid derivative shown by the general formula [3] and carboxylic acid compound shown by the general formula [4] or the salt thereof.

The temperature of the reaction of the (meth) acrylic acid derivative shown by the general formula [3] with the carboxylic acid compound shown by the general formula [4] or the salt thereof may be set appropriately according to the reaction solvent, etc., and, usually it is 20 to 120° C., preferably 40 to 80° C., and the reaction time is usually 1 to 20 hours, preferably 5 to 12 hours.

The polymerization reaction in the method for production of the polymer which has a monomer unit shown by the general formula [1] can be performed by a method well known per se such as, for example, solution polymerization, mass polymerization, emulsification polymerization, and suspension polymerization. As a polymerization initiator, for example, azo compounds such as azoisobutyronitrile, 2,2'-azobis(2,4-dimethylvaleronitril), 2,2'-azobis(methyl 2-methylpropionate), 2,2'-azobis(2-methylbutyronitril), peroxides such as benzoyl peroxide, lauroyl peroxide, potassium peroxodisulfate, and ammonium peroxodisulfate, can be employed, and, peroxides are desirable, and among them, ammonium peroxodisulfate is particularly preferable. The usage of polymerization initiator is usually 0.1 to 3% by weight for the total weight of total monomers. In said polymerization reaction, it is desirable to carry out the reaction under the atmosphere of inert gas such as nitrogen, argon, and the polymerization temperature is usually 40 to 120° C., preferably 50 to 70° C., and the polymerization time is 1 to 20 hours, preferably 0.5 to 5 hours. The solvent to be used here includes water along with the above specific examples of the reaction solvent at the reaction of the (meth) acrylic acid derivative shown by the general formula [3] with the carboxylic acid compound shown by the general formula [4] or the salt thereof, and, water is preferable. The amount of solvent to be used is usually 30 to 360 mL for 20 g of the total weight of polymer.

As a specific method for producing homopolymer which has monomer unit shown by the general formula [1], for example, first of all, 1 mole of the (meth) acrylic acid derivative shown by the above-described general formula [3] is reacted with 1 to 2 moles of the carboxylic acid compound shown by the general formula [4] or the salt thereof in 500 to 1000 mL of ethanol at 40 to 80° C. for 5 to 12 hours to obtain the monomer. Subsequently, 10 g of the obtained monomer is dissolved in 50 to 100 mL of water, and by adding 1 to 30 mg of the peroxide to said solution, and polymerization reaction is carried out under argon atmosphere at 50 to 70° C. for 1 to 20 hours.

(3) A Copolymer which has a Monomer Unit Shown by the General Formula [1] and a Monomer Unit Shown by the General Formula [2]

Content of the monomer unit shown by the general formula [1] in said copolymer is usually 50% by mole or more and less than 100% by mole, and 50 to 95% by mole is preferable, and 50 to 60% by mole is more preferable. In addition, the content of the monomer unit shown by the general formula [2] in said copolymer is usually more than 0% by mole and 50% by mole or less, preferably it is 5 to 50% by mole, and more preferably it is 40 to 50% by mole.

Specific example of the monomer unit shown by the general formula [1] includes the same one as described in the paragraph of homopolymer which has a monomer unit shown by the general formula [1] in the above (1), and preferable one is also the same.

$R_4$ in the general formula [2] represents a hydrogen atom or a methyl group, and, a hydrogen atom is preferable.

"k" in the general formula [2] is usually 1 to 10, and, 4 to 8 is preferable, and 6 to 8 is more preferable.

Specific example of the monomer unit shown by the general formula [2] includes, for example, the general formula [2-1] and [2-2], and, the general formula [2-1] is preferable.

(Wherein, k is the same as describe above)

(Wherein k is the same as describe above)

Among them, the following general formula [2-1-1]

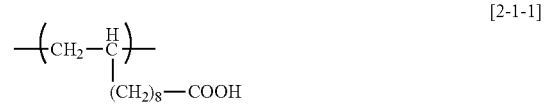

is preferable.

Combination of the monomer unit shown by the general formula [1] and the monomer unit shown by the general formula [2] includes, for example,

| Polymer No. | Monomer unit shown by general formula [1] | Monomer unit shown by general formula [2] |
| --- | --- | --- |
| P-1 | General formula [1-1] | General formula [2-1] |
| P-2 | General formula [1-2] | General formula [2-1] |
| P-3 | General formula [1-3] | General formula [2-1] |
| P-4 | General formula [1-4] | General formula [2-1] |
| P-5 | General formula [1-5] | General formula [2-1] |
| P-6 | General formula [1-6] | General formula [2-1] |
| P-7 | General formula [1-1] | General formula [2-2] |
| P-8 | General formula [1-2] | General formula [2-2] |
| P-9 | General formula [1-3] | General formula [2-2] |
| P-10 | General formula [1-4] | General formula [2-2] |
| P-11 | General formula [1-5] | General formula [2-2] |
| P-12 | General formula [1-6] | General formula [2-2], | and preferable combinations are

| Polymer No. | Monomer unit shown by general formula [1] | Monomer unit shown by general formula [2] |
| --- | --- | --- |
| P-1 | General formula [1-1] | General formula [2-1] |
| P-3 | General formula [1-3] | General formula [2-1] |
| P-4 | General formula [1-4] | General formula [2-1], | among them, the combination whose monomer unit shown by the general formula [1] is the one which is shown by [1-1-1], [1-1-2], [1-3-1] or [1-4-1], and whose monomer unit shown by the general formula [2] is [2-1-1], is more preferable, and the combination whose monomer unit shown by the general formula [1] is [1-1-1], and whose monomer unit shown by the general formula [2] is [2-1-1] is particularly preferable.

(4) Method for Production of a Copolymer which has a Monomer Unit Shown by the General Formula [1] and a Monomer Unit Shown by the General Formula [2]

As the method for production of a copolymer which has a monomer unit shown by the general formula [1] and a monomer unit shown by the general formula [2], for example, it can be produced by polymerizing a monomer shown by the following general formula [1'],

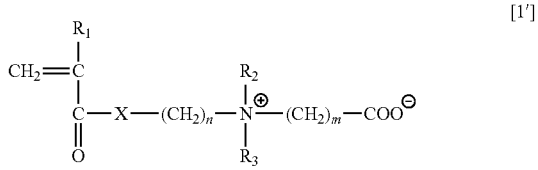

[1']

(Wherein $R_1$, $R_2$, $R_3$, X, n and m are the same as described above.), and a vinyl compound shown by the general formula [2']

[2']

(Wherein $R_4$ and k are the same as described above) by polymerization reaction according to a method well known per se, for example, a method described in JP-A-52-27713.

Specific example and preferable specific example of the monomer shown by the general formula [1'] include the one which is in conformity to the monomer unit shown by the above-described general formula [1]. In addition, the monomer shown by the general formula [1'] can be obtained by the reaction of the (meth) acrylic acid derivative shown by the general formula [3] with the carboxylic acid compound shown by the general formula [4] or the salt thereof described in the paragraph of the method for production of a homopolymer which has monomer unit shown by the general formula [1].

Specific example of the vinyl compound shown by the general formula [2'] includes, for example, 4-pentenoic acid, 5-hexenoic acid, 6-heptenoic acid, 7-octenoic acid, 8-nonenoic acid, 9-decenoic acid, 10-undecenoic acid, 4-methyl-4-pentenoic acid, 5-methyl-5-hexenoic acid, 6-methyl-6-heptenoic acid, 7-methyl-7-octenoic acid, 8-methyl-8-nonenoic acid, 9-methyl-9-decenoic acid, 10-methyl-10-undecenoic acid etc., and, 7-octenoic acid, 8-nonenoic acid, 9-decenoic acid, 10-undecenoic acid etc. are preferable, and among them, 10-undecenoic acid is preferable especially.

For these vinyl compounds, commercially available products or the one which is synthesized appropriately from alkyl halide compound by a routine procedure may be employed.

The usage of the vinyl compound shown by the above-described general formula [2'] is usually 1 to 100% by mole, preferably 3 to 100% by mole, more preferably 50 to 100% by mole for the amount of the monomer shown by the general formula [1'].

A condition of the polymerization reaction of the monomer shown by the above-described general formula [1'] with the vinyl compound shown by the general formula [2'] includes the same one as polymerization reaction in the method for production of a polymer which has a monomer unit shown by the above-described general formula [1], and preferable one is also the same.

The method for production of a copolymer which has a monomer unit shown by the general formula [1] and a monomer unit shown by the general formula [2] is specifically performed as mentioned below. One mole of the monomer shown by the general formula [1'] and 0.01 to 1 mole of the vinyl compound shown by the above-described general formula [2'] are dissolved in a 50 to 100 mL of mixed solution of water and DMF (1:2 to 2:1 as volume ratios), and followed by adding to the solution 0.1 to 3% by weight of peroxide for the total weights of the above-described monomer and vinyl compound. Then, a polymerization reaction is carried out under argon atmosphere at 50 to 70° C. for 1 to 20 hours.

(5) The Agglutination Enhancer, the Immunoagglutination Measurement Method, And the Reagent for Immunoagglutination Measurement Method of the Present Invention The agglutination enhancer of the present invention comprises a polymer which has a monomer unit shown by the general formula [1] as described above, and more specifically, it comprises a homopolymer which has a monomer unit shown by the above-described general formula [1] or a copolymer which has a monomer unit shown by the above-described general formula [1] and a monomer unit shown by the general formula [2]. Said agglutination enhancer is preferably used by being dissolved in a reagent which is employed in the turbidimetric immunoassay among the immunoagglutination measurement methods, and among them, it is particularly preferable to be used by being dissolved in a reagent for the latex agglutination method which employs the latex as a carrier.

In the immunoagglutination measurement method of the present invention, the above-described agglutination enhancer of the present invention is used by adding it so that its concentration in the reaction solution is usually 0.1 to 8 w/v %, preferably 0.1 to 4 w/v %, more preferably 0.1 to 2 w/v %. In addition, said concentration is preferably changed its setting according to the analyte, and for example, in the case where the analyte is CRP and Fer, the agglutination enhancer is used by adding it so that its concentration in the reaction solution is usually 0.1 to 8 w/v %, preferably 0.1 to 4 w/v %, more preferably 0.1 to 1 w/v %. For example, in the case where the analyte is PSA, the agglutination enhancer is used by adding it so that its concentration in the reaction solution is usually 0.1 to 7 w/v %, preferably 0.1 to 4 w/v %, more preferably 0.1 to 2 w/v %.

Except for carrying out the antigen-antibody reaction in the coexistence of the agglutination enhancer of the present invention, the immunoagglutination measurement method of the present invention may be performed according to the method of operation well known per se using various kinds of reagents which are used in the immunoagglutination measurement method well known per se (such as turbidimetric immunoassay, nephelometric immunoassay) which perform the measurement of analyte based on the agglutination etc. derived from the antigen-antibody reaction. For example, it may be performed by carrying out the antigen-antibody reaction in the coexistence of the above-described agglutination enhancer of the present invention by bringing an antibody against the analyte or an antigen for the analyte contact with the analyte. More specifically, it may be performed by carrying out the antigen-antibody reaction in the coexistence of the above-described agglutination enhancer of the present invention by bringing an antibody against the analyte or a carrier supporting the antibody, or by bringing an antigen against the analyte or a carrier supporting the antigen into contact with the analyte. The agglutination enhancer of the present invention in the above-described method may be coexisted at the above-described concentration in the reaction solution. As a specific method except for coexistence of the above-described agglutination enhancer of the present invention, for example, when a method for measuring scattered light (nephelometry) is used, it may be carried out, for example, according to the method described in "Manual of Clinical Laboratory Medicine", 30th edition, 2nd printing, p. 851-853 (1993), Kanehara & Co., Ltd. When a method for measuring transmitted light (turbidimetric immunoassay) is used, it may be carried out similarly according to the method described in the "Manual of Clinical Laboratory Medicine", 30th edition, 2nd printing, p. 853-854 (1993), Kanehara & Co., Ltd., etc. Further, when the latex agglutination method, in which the degree of agglutination of sensitized latex to an antibody against the analyte or an antigen for the analyte is measured based on the variation of the scattered light or transmitted light, and based on the results, measurement of the analyte is performed, is used, it may be carried out, for example, according to the method described in "New Case Example of Utilization of Immunoassay Method and Application to Diagnostic Reagent•Development of Therapeutic Agent" (KEIEI KYOUIKU SYUPPANSYA) p. 103-187, etc.

The buffer to be used at the reaction of the immunoagglutination measurement method of the present invention includes all the buffers usually to be used for the turbidimetric immunoassay and nephelometric immunoassay, such as, specifically, for example, Tris buffer, phosphate buffer, Veronal buffer, borate buffer and Good's buffer, and pH at the measurement reaction is not limited specifically as long as it is in a range where the antigen-antibody reaction is not restrained. It is usually selected suitably from a range between pH 6 and pH 10.

The measurement in the immunoagglutination measurement method of the present invention is performed by measuring scattered light or transmitted light, and the measurement may be carried out with the use of biochemical general-purpose equipment such as automated analyzer, spectrophotometer, and dedicated equipment for nephelometry measurement such as laser nephelometer.

The measurement object component, which can be measured by the immunoagglutination measurement method of the present invention, may be the one which can be measured by utilizing the antigen-antibody reaction, and it includes, for example, C-reactive protein (CRP), immunoglobulin G (IgG), immunoglobulin A (IgA), immunoglobulin M (IgM), immunoglobulin E (IgE), ASO (anti-streptolysin O), albumin, microalbumin, prealbumin, complement3 (C3), complement4 (C4), transferrin, haptoglobin, lipoprotein (a) (LP(a)), apolipoprotein A-I (ApoAI), apolipoprotein A-II (ApoAII), apolipoprotein B (ApoB), apolipoprotein C-II (ApoCII), apolipoprotein C-III (ApoCIII), apolipoprotein E (ApoE), rheumatoid factor (RF), prostate specific antigen (PSA), ferritin (Fer), beta$_2$-microalbumin ($\beta_2$-m), myoglobin (Mb), pepsinogen (PG), hyaluronic acid (HA), creatine kinase MB isozyme (CK-MB), TP antibody, syphilis lipid antibody, *Helicobacter pylori* antigen and antibody, HCV antigen and antibody, HBs antigen and antibody, HIV antigen and antibody, cystatin C, matrix metalloproteinase-3 (MMP-3), KL-6, alpha-fetoprotein (AFP), carcinoembryonic antigen (CEA), insulin and C-peptide etc., which are contained in a biological sample such as, for example, serum, plasma, urine, lymph and cerebrospinal fluid, and among them, CRP, Fer, PSA, or CK-MB is preferable. It should be noted that, when the CK-MB is a measuring object, it is preferable to employ an agglutination enhancer comprising a copolymer which has a monomer unit shown by the general formula [1] and a monomer unit shown by the following general formula [2].

The reagents for the immunoagglutination measurement method of the present invention may be the one which comprises the above-described agglutination enhancer of the present invention, and its content is usually 0.1 to 10 w/v %, preferably 0.1 to 5 w/v %, and more preferably 0.1 to 2 w/v % as a concentration in the reagent. In addition, said concentration is preferable to change according to the analyte, and for example, in the case where the analyte is CRP and Fer, it is usually 0.1 to 10 w/v %, preferably 0.1 to 5 w/v %, more preferably 0.1 to 1 w/v %, and for example, in the case where the analyte is PSA, it is usually 0.1 to 10 w/v %, preferably 0.1 to 5 w/v %, more preferably 0.1 to 2 w/v %. In said reagent, beyond that, for example, in the case where the analyte is an antigen, it may comprise an antibody or an appropriate carrier (for example, latex and the like) supporting said antibody, or in the case where the analyte is an antibody, it may comprise an antigen or an appropriate carrier (for example, latex and the like) supporting said antigen. In addition, said reaction regent may have buffer (for example, Tris buffer, phosphate buffer, Veronal buffer, borate buffer, Good's buffer, etc.), stabilizing agent (for example, albumin, globulin, water-soluble gelatin, surface active agent, carbohydrates, etc.), preservatives (for example, salicylic acid, benzoic acid, sodium azide, etc.), and other substances which are usually used in this field and do not disturb stability of coexisting reagent, nor inhibit antigen-antibody reaction. The concentration thereof may also be used within the range usually used in this field.

The measuring object in the reagent for immunoagglutination measurement method of the present invention includes the same one as described in the paragraph of the immunoagglutination measurement method of the present invention, and preferable one is also the same.

Hereinafter, the present invention will be explained by Examples, however, the present invention is not limited thereto in any way.

EXAMPLE

Synthetic Example 1: Synthesis of Polymer 1 to 3

(1) Synthesis of N-[2-(carboxymethyldimethylamino) ethyl] methacrylate (Monomer A)

Potassium hydroxide (297 g, 4.5 moles) was dissolved in 1.6 L of ethanol, then chloroacetatic acid (426 g, 4.5 moles, produced by Wako Pure Chemical Industries Ltd.) was added to said solution, after that the reaction was carried out under agitation at room temperature for 2 hours. Subsequently, crystals deposited by the reaction were recovered by filtration and washed with isopropanol. Furthermore, after the washed crystals were suspended in 1 L of isopropanol, N-[2-(dimethylamino) ethyl]methacrylate (475 g, 3.0 moles, produced by Wako Pure Chemical Industries Ltd.) was added to said suspension, and then reaction was carried out under agitation and under reflux for 12 hours. After completion of the reaction, insoluble material was separated by filtration and washed with isopropanol to recover the wash solution. After the filtrate and the wash solution were combined and dried under reduced pressure, acetone was added to the obtained residue to precipitate crystals. After that, the crystals deposited were recovered by filtration and dried under reduced pressure to obtain 420 g of N-[2-

(carboxymethyldimethylamino) ethyl]methacrylate (hereinafter, abbreviated as monomer A):

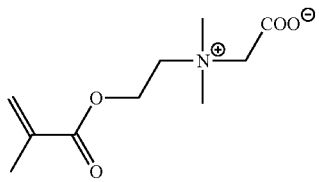

(2) Synthesis of Polymer 1 to 3

After the monomer A obtained in the above-described (1) (11 g to 22 g) was dissolved in ion-exchanged water (90 mL to 189 mL), argon gas substitution was carried out for 5 to 30 minutes. To this solution, 2 mL of 10% ammonium peroxodisulfate solution was added, and then reacted under agitation at 50° C. for 1 to 2 hours. After completion of the reaction, said reaction solution was purified using a dialysis tube [Spectra/Por 2 (molecular weight cut off: 12K to 14K, produced by Spectrum Laboratories, Inc.), ion-exchanged water; 5 L×3 times]. The above-described operation was carried out for 3 times, and the obtained polymer solution was lyophilized respectively and polymer 1 to 3 (9.4 g to 14.8 g) were obtained.

With respect to the polymer 1 to 3, the presence of methacrylic acid segment (0.84 ppm to 1.32 ppm) was identified by $^1$H-NMR spectrometry, and the presence of carbonyl group (—C=O) (1725 cm$^{-1}$) was identified by IR spectrometry, respectively.

Physical property of the polymer 1 to 3 were examined by way of GPC (Shodex SB-806M-HQ, produced by SHOWA DENKO K.K.), and the results were shown in the following table.

|  | Weight-average molecular weight | Molecular weight distribution |
| --- | --- | --- |
| Polymer 1 | 64,240 | 4.279 |
| Polymer 2 | 121,752 | 2.984 |
| Polymer 3 | 2,644,350 | 5.234 |

Synthetic Example 2: Synthesis of Polymer 4

(1) Synthesis of N-(4-dimethylamino) butyl methacrylate

N-(4-dimethylamino) butanol (23 g, 0.2 moles, produced by Wako Pure Chemical Industries Ltd.) was dissolved in 200 mL of chloroform, and methacrylic acid chloride (25 g, 0.24 moles, produced by Wako Pure Chemical Industries Ltd.) was added to this solution under cooling on ice, and then reacted while agitating at room temperature for 1.5 hours. Subsequently, the obtained reaction solution was washed with saturated aqueous sodium bicarbonate and saturated aqueous sodium chloride, and then dried over magnesium sulfate. After that, the magnesium sulfate was removed by filtration, and the obtained filtrate was concentrated by reduced pressure to obtain 38 g of N-(4-dimethylamino) butyl methacrylate.

(2) Synthesis of N-[4-(carboxymethyldimethylamino) butyl] methacrylate (Monomer B)

Potassium hydroxide (12 g, 0.21 moles) was dissolved in 150 mL of ethanol, and chloroacetic acid (20 g, 0.21 moles, produced by Wako Pure Chemical Industries Ltd.) was added, and then reacted under agitation at room temperature for 2 hours. Subsequently, crystals generated by the reaction were recovered by filtration, and washed with ethanol. After that, the washed crystals were suspended in 50 mL of ethanol, and N-(4-dimethylamino) butyl methacrylate (38 g, 0.2 moles) obtained in the above-described (1) was added to the suspension, and then, reacted under agitation and under reflux for 12 hours. After completion of the reaction, insoluble material was separated by filtration and washed with ethanol to recover said wash solution. After the filtrate and the wash solution were mixed and dried under reduced pressure, acetone was added to the obtained residue to precipitate crystals. After that, the insoluble material deposited was separated by filtration and concentrated under reduced pressure to obtain 26 g of N-[4-(carboxymethyldimethylamino) butyl methacrylate (hereinafter, abbreviated as monomer B):

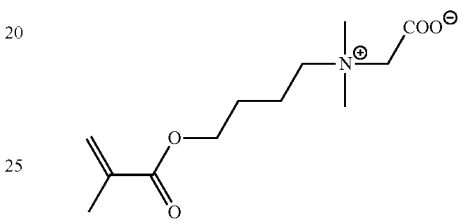

(3) Synthesis of Polymer 4

Monomer B (25 g) obtained in the above-described (2) was dissolved in 90 mL of ion-exchanged water, and then argon gas substitution was carried out for 30 minutes. Ammonium peroxodisulfate solution (2 mL, 10%) was added to this solution, and then reacted under agitation at 50° C. for 2 hours. After completion of the reaction, the reaction solution was purified using a dialysis tube [Spectra/Por 2 (molecular weight cut off: 12K to 14K, produced by Spectrum Laboratories, Inc.), ion-exchanged water; 5 L×3 times]. After purification, the obtained polymer solution was lyophilized, and polymer 4 (17.2 g) was obtained.

With respect to the polymer 4, the presence of methacrylic acid segment (0.84 ppm to 1.45 ppm) was identified by $^1$H-NMR spectrometry, and the presence of carbonyl group (—C=O) (1725 cm$^{-1}$) was identified by IR spectrometry, respectively.

Physical property of the polymer 4 was examined by way of GPC (Shodex SB-806M-HQ, produced by SHOWA DENKO K.K.). As a result, it was determined that the weight-average molecular weight was 807,920, and the molecular weight distribution was 3.895.

Synthetic Example 3: Synthesis of Polymer 5

(1) Synthesis of N-[3-(carboxymethyldimethylamino) propyl]acrylamide (Monomer C)

Potassium hydroxide (198 g, 3.0 moles) was dissolved in 1 L of ethanol, and chloroacetatic acid (284 g, 3.0 moles, produced by Wako Pure Chemical Industries Ltd.) was added to this solution, and then the reaction was carried out under agitation at room temperature for 2 hours. Subsequently, the crystals generated by the reaction were recovered by filtration and washed with isopropanol. After that, the washed crystals were suspended in 400 mL of isopropanol, and N-[3-(dimethylamino) propyl]acrylamide (511 g, 3.0 moles, produced by Wako Pure Chemical Industries Ltd.) was added to this suspension, and then reacted under agitation and under reflux for 12 hours. After completion of the reaction, insoluble material was separated by filtration and washed with isopropanol to recover the wash solution. After the filtrate and the wash solution were combined and dried under reduced pressure, acetone was added to the obtained residue to precipitate the crystals. After that, the deposited crystals were recovered by filtration and dried under reduced pressure to obtain 565 g of N-[3-(carboxymethyldimethylamino) propyl]acrylamide (hereinafter, abbreviated as monomer C):

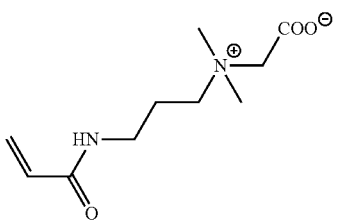

(2) Synthesis of Polymer 5

Monomer C (46 g) obtained in the above-described (1) was dissolved in 90 mL of ion-exchanged water, and then argon gas substitution was carried out for 30 minutes. Subsequently, 2 mL of 10% ammonium peroxodisulfate solution was added to this solution, and then reacted under agitation at 50° C. for 2 hours. After completion of the reaction, the reaction solution was purified using a dialysis tube [Spectra/Por 2 (molecular weight cut off: 12K to 14K, produced by Spectrum Laboratories, Inc.), ion-exchanged water; 5 L×3 times]. After purification, the obtained polymer solution was lyophilized, and polymer 5 (26.2 g) was obtained.

With respect to the polymer 5, the presence of methacrylic acid segment (1.13 ppm to 2.05 ppm) was identified by $^1$H-NMR spectrometry, and the presence of amide group (—NH—C=O) (1640 cm$^{-1}$, 1540 cm$^{-1}$) was identified by IR spectrometry, respectively.

Physical property of the polymer 5 was examined by way of GPC (Shodex SB-806M-HQ, produced by SHOWA DENKO K.K.). As a result, it was determined that the weight-average molecular weight was 262,065, and the molecular weight distribution was 4.332.

Synthetic Example 4: Synthesis of Polymer 6

(1) Synthesis of N-[3-(carboxymethyldimethylamino) propyl]methacrylamide (Monomer D)

Potassium hydroxide (198 g, 3.0 moles) was dissolved in 1 L of ethanol, and chloroacetatic acid (284 g, 3.0 moles, produced by Wako Pure Chemical Industries Ltd.) was added to this solution, and then the reaction was carried out under agitation at room temperature for 2 hours. Subsequently, the crystals generated by the reaction were recovered by filtration and washed with isopropanol. After that, the washed crystals were suspended in 400 mL of isopropanol, and N-[3-(dimethylamino) propyl]methacrylamide (511 g, 3.0 moles, produced by Wako Pure Chemical Industries Ltd.) was added to this suspension, and then reacted under agitation and under reflux for 12 hours. After completion of the reaction, insoluble material was separated by filtration and washed with isopropanol to recover the wash solution. After the filtrate and the wash solution were combined and dried under reduced pressure, acetone was added to the obtained residue to precipitate crystals. After that, the deposited crystals were recovered by filtration and dried under reduced pressure to obtain 565 g of N-[3-(carboxymethyldimethylamino) propyl]methacrylamide (hereinafter, abbreviated as monomer D):

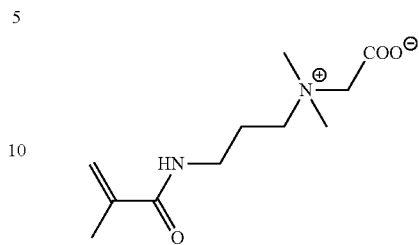

(2) Synthesis of Polymer 6

Monomer D (21 g) obtained in the above-described (1) was dissolved in 90 mL of ion-exchanged water, and then argon gas substitution was carried out for 30 minutes. Subsequently, to this solution, 2 mL of 10% ammonium peroxodisulfate solution was added, and then reacted under agitation at 50° C. for 2 hours. After completion of the reaction, the reaction solution was purified using a dialysis tube [Spectra/Por 2 (molecular weight cut off: 12K to 14K, produced by Spectrum Laboratories, Inc.), ion-exchanged water; 5 L×3 times]. After the purification, the obtained polymer solution was lyophilized, and polymer 6 (13.5 g) was obtained.

With respect to the polymer 6, the presence of methacrylic acid segment (1.10 ppm to 2.00 ppm) was identified by $^1$H-NMR spectrometry, and the presence of amide group (—NH—C=O) (1640 cm$^{-1}$, 1540 cm$^{-1}$) was identified by IR spectrometry, respectively.

Physical property of the polymer 6 was examined by way of GPC (Shodex SB-806M-HQ, produced by SHOWA DENKO K.K.). As a result, it was determined that the weight-average molecular weight was 407,359, and the molecular weight distribution was 2.375.

Synthetic Example 5: Synthesis of Copolymer 1

Monomer A (22 g) obtained in the above-described Synthetic Example 1 and 10-undecenoic acid (1.8 g, produced by Wako Pure Chemical Industries Ltd.) were dissolved in a mixed solvent of 50 mL of ion-exchanged water and 40 mL of DMF, and then argon gas substitution was carried out for 30 minutes. Subsequently, 2 mL of 10% ammonium peroxodisulfate solution was added to this solution, and then reacted under agitation at 50° C. for 2 hours. After completion of the reaction, the reaction solution was purified using a dialysis tube [Spectra/Por 2 (molecular weight cut off: 12K to 14K, produced by Spectrum Laboratories, Inc.), ion-exchanged water; 5 L×3 times]. After purification, the obtained polymer solution was lyophilized, and copolymer 1 (16.2 g) was obtained. In addition, the copolymer 1 comprises 40% by mole of undecenoic acid derived monomer unit (hereinafter, abbreviated as monomer unit E).

With respect to the copolymer 1, the presence of the monomer unit derived from methacrylic acid (1.10 ppm to 2.00 ppm) and the monomer unit derived from undecenoic acid (1.03 ppm) were identified by $^1$H-NMR spectrometry, and the presence of carbonyl group (—C=O) (1725 cm$^{-1}$) was identified by IR spectrometry, respectively.

Physical property of the copolymer 1 was examined by way of GPC (Shodex SB-806M-HQ, produced by SHOWA DENKO K.K.). As a result, it was determined that the weight-average molecular weight was 658,206, and the molecular weight distribution was 2.216.

Synthetic Example 6: Synthesis of Copolymer 2

Monomer A (22 g) obtained in the above-described Synthetic Example 1 and 10-undecenoic acid (7.4 g, produced by Wako Pure Chemical Industries Ltd.) were dissolved in a mixed solvent of 50 mL of ion-exchanged water and 40 mL of DMF, and then argon gas substitution was carried out for 30 minutes. Subsequently, 2 mL of 10% ammonium peroxodisulfate solution was added to this solution, and then reacted under agitation at 50° C. for 2 hours. After completion of the reaction, the reaction solution was purified using a dialysis tube [Spectra/Por 2 (molecular weight cut off: 12K to 14K, produced by Spectrum Laboratories, Inc.), ion-exchanged water; 5 L×3 times]. After the purification, the obtained polymer solution was lyophilized, and copolymer 2 (19.4 g) was obtained. In addition, the copolymer 2 comprises 5% by mole of monomer unit E.

With respect to the copolymer 2, the presence of methacrylic acid segment (1.10 ppm to 2.00 ppm) and undecenoic acid segment (1.03 ppm) were identified by $^1$H-NMR spectrometry, and the presence of carbonyl group (—C=O) (1725 cm$^{-1}$) was identified by IR spectrometry, respectively. Physical property of the copolymer 2 was examined by way of GPC (Shodex SB-806M-HQ, produced by SHOWA DENKO K.K.). As a result, it was determined that the weight-average molecular weight was 957,680, and the molecular weight distribution was 2.041.

Example 1: Measurement of CRP by Latex Immunoagglutination Measurement Method Using Polymers with Different Molecular Weight as an Immunoagglutination Enhancer (1) Preparation of Anti-Human CRP Antibody-Sensitized (Immobilized) Latex Reagent Borate buffer solution (4.5 mL, 50 mM, pH 7.5) containing 1 mg/mL of anti-human CRP goat polyclonal antibody (produced by Oriental Yeast Co., Ltd.) was mixed with 0.5 mL of 10 w/v % aqueous solution of polystyrene latex with 0.12 μm in particle size (produced by Nippon Paint Co., Ltd.), and reacted at 7° C. overnight. Then, 5 mL of the obtained suspension was mixed with borate buffer solution (5 mL, 50 mM, pH7.5) containing 2.5 w/v % bovine serum albumin (BSA), and reacted at 7° C. for 2 hours. Subsequently, whole quantity of the latex separated by centrifugal separation (45,000×g, 30 minutes) was washed with borate buffer solution (5 mL, 50 mM, pH7.5), then suspended in borate buffer solution (12.5 mL, 50 mM, pH7.5) containing 0.5 w/v % BSA, and used said suspension as an anti-human CRP antibody-sensitized latex solution 1). In addition, the one which was prepared by the same way as described above using polystyrene latex with 0.2 μm in particle size (produced by Nippon Paint Co., Ltd.) was used as an anti-human CRP antibody-sensitized latex solution 2).

(2) Sample

Saline (0.85% NaCl) was used for a blank sample. As the sample, LT•CRP-HS Calibrator Set HO (manufactured by Wako Pure Chemical Industries Ltd., and CRP concentration thereof is 0.2 mg/dL, 1.0 mg/dL, 4.0 mg/dL, 18.0 mg/dL, and 35.0 mg/dL, respectively) was used.

(3) Reagent

First Reagent

Tris buffer solutions (0.1 M, pH 8.0), which contain 0.4 w/v % of polymer 1, polymer 2 or polymer 3 synthesized in Synthetic Example 1 as an agglutination enhancer, and include 0.1% BSA and 1% NaCl, were prepared, and thus three kinds of first reagents were prepared.

Second Reagent

The anti-human CRP (12 mL) antibody-sensitized latex 1) and the anti-human CRP (8 mL) antibody-sensitized latex 2) which were prepared in the above-described (1) were mixed, and used as a second reagent.

(4) Measurement Method

Using BM-8 Autoanalyzer (manufactured by JEOL Ltd.), the CRP concentration in a sample was measured using the above-described sample, the above-described first reagent and the above-described second reagent under the following condition:

Sample: 7.5 μL (diluted five fold with saline);
First reagent: 100 μL;
Second reagent: 25 μL;
Measurement method: 2 point-end method (34 to 65);
Dominant wavelength: 596 nm.

The obtained results were shown in Table 1.

Comparative Example 1: Measurement of CRP by Latex Immunoagglutination Measurement Method Using Conventional Immunoagglutination Enhancer The CRP was measured by the same method as described in Example 1 except for using 0.1 M Tris buffer solution (pH 8.0) which contains 0.4 w/v % of polyethylene glycol 6,000 (PEG 6,000, produced by Wako Pure Chemical Industries Ltd.) or MPC polymer (produced by NOF Corporation) instead of polymer 1 to 3 of Example 1 as an agglutination enhancer, and includes 0.1% BSA and 1% NaCl. The results were shown in Table 1 in conjunction with the results of Example 1.

TABLE 1

| | Example 1 | | | Comparative Example 1 | |
|---|---|---|---|---|---|
| | Agglutination enhancer | | | | |
| | Polymer 1 | Polymer 2 | Polymer 3 | PEG | MPC |
| | | | MW | | |
| CRP concentration | 64,340 | 121,752 | 2,644,000 | 6,000 | 245,000 |
| Blank | 51 | 51 | 45 | 47 | 51 |
| 0.2 mg/dL | 360 | 452 | 523 | 189 | 230 |
| 1.0 mg/dL | 1299 | 1516 | 1758 | 733 | 936 |
| 4.0 mg/dL | 2427 | 2703 | 2982 | 1686 | 2038 |
| 18.0 mg/dL | 5540 | 6298 | 6911 | 3900 | 4711 |
| 35.0 mg/dL | 7187 | 8128 | 8623 | 4945 | 6883 |

From the results shown in Table 1, it turned out that, in the CRP measurement system, all of polymer 1, 2, and 3 showed higher agglutination enhancing effect than PEG 6,000 and MPC of Comparative Example 1 which were conventional agglutination enhancers. In addition, it turned out that the polymer with higher molecular weight showed the more excellent effect.

Example 2: Measurement of Fer by Latex Immunoagglutination Measurement Method Using Polymers with Different Molecular Weight as an Immunoagglutination Enhancer (1) Preparation of Anti-Human Fer Antibody-Sensitized (Immobilized) Latex Reagent Borate buffer solution (1 mL, 50 mM, pH 7.5) containing 0.6 mg/mL of anti-human Fer rabbit polyclonal antibody (produced by Dako Corporation) was mixed with borate buffer solution (1 mL, 50 mM, pH 7.5) in which polystyrene latex with 0.3 μm in particle size (produced by Sekisui Chemical Co., Ltd.) was suspended so as to provide 2 w/v %, and reacted at 25° C. for 2 hours. Then, 2 mL of the obtained suspension was mixed with borate buffer solution (2 mL, 50 mM, pH7.5) containing 1.25 w/v % BSA, and reacted at 7° C. for 2 hours. Subsequently, whole quantity of the latex separated by centrifugal separation (45,000×g, 30 minutes) was washed with borate buffer solution (4 mL, 50 mM, pH7.5), then suspended in borate buffer solution (20 mL, 50 mM, pH7.5) containing 0.5 w/v % BSA, and used it as an anti-human Fer antibody-sensitized latex solution.

(2) Sample

Saline (0.85% NaCl) was used for a reagent blank test sample. As the sample, Ferritin Calibrator Set (manufactured by Wako Pure Chemical Industries Ltd.; which includes those with Fer concentration, 30 ng/mL, 100 ng/mL, 200 ng/mL, 500 ng/mL, and 1000 ng/mL, respectively) was used.

(3) Reagent

First Reagent

HEPES-NaOH buffer solutions (0.1 M, pH 7.0), which contain 0.4 w/v % of polymer 1, polymer 2 or polymer 3 synthesized in Synthetic Example 1 as an agglutination enhancer, and include 0.1% BSA and 1% NaCl, were prepared, and thus three kinds of first reagents were prepared.

Second Reagent

The anti-human Fer antibody-sensitized latex solution prepared in the above-described (1) was used as a second reagent.

(4) Measurement Method

Using BM-8 Autoanalyzer (manufactured by JEOL Ltd.), the Fer concentration in a sample was measured using above-described sample, above-described first reagent and above-described second reagent under the following condition:

Sample: 12 μL (diluted double with saline);

First reagent: 90 μL;

Second reagent: 30 μL;

Measurement method: 2 point-end method (35 to 59);

Dominant wavelength: 694 nm.

The obtained results were shown in Table 2.

Comparative Example 2: Measurement of Fer by Latex Immunoagglutination Measurement Method Using Conventional Immunoagglutination Enhancer The Fer was measured by the same method as described in Example 2 except for using HEPES buffer solution (0.1 M, pH 8.0) which contains 0.4 w/v % of polyethylene glycol 6,000 (PEG 6,000, produced by Wako Pure Chemical Industries Ltd.) or MPC polymer (produced by NOF Corporation) instead of polymer 1 to 3 of Example 2 as an agglutination enhancer, and includes 0.1% BSA and 1% NaCl.

The results were shown in Table 2 in conjunction with the results of Example 2.

TABLE 2

|  | Example 2 | | | Comparative Example 2 | |
|---|---|---|---|---|---|
|  | Agglutination enhancer | | | | |
|  | Polymer 1 | Polymer 2 | Polymer 3 | PEG | MPC |
| Fer concentration | 64,340 | 121,752 | 2,644,000 | 6,000 | 245,000 |
| 0 ng/mL (Blank) | −32 | −39 | −21 | −26 | −29 |
| 30 ng/mL | 95 | 117 | 115 | 40 | 66 |
| 100 ng/mL | 406 | 483 | 512 | 201 | 291 |
| 200 ng/mL | 792 | 978 | 1070 | 438 | 609 |
| 500 ng/mL | 2206 | 2677 | 2894 | 1115 | 1553 |
| 1000 ng/mL | 3439 | 3814 | 3913 | 2074 | 2767 |

From the results shown in Table 2, it turned out that, in the Fer measurement system, all of polymer 1, 2, and 3 showed higher agglutination enhancing effect than PEG 6,000 and MPC of Comparative Example 2. Moreover, it turned out that, as is the case with CRP measurement system, the polymer with higher molecular weight showed the more excellent effect.

Example 3: Measurement of PSA by Latex Immunoagglutination Measurement Method Using Polymers with Different Molecular Weight as an Immunoagglutination Enhancer (1) Preparation of Anti-Human PSA Antibody-Sensitized (Immobilized) Latex Reagent Borate buffer solution (1 mL, 50 mM, pH 7.1) containing 0.6 mg/mL of anti-human PSA monoclonal antibody (Clone No. PSA10; produced by Wako Pure Chemical Industries Ltd.) was mixed with borate buffer solution (1 mL, 50 mM, pH 7.1) in which polystyrene latex with 0.28 μm in particle size (produced by Sekisui Chemical Co., Ltd.) was suspended so as to provide 2 w/v %, and reacted at 25° C. for 2 hours. Then, whole quantity of the latex separated from the aforementioned suspension by centrifugal separation (45,000×g, 30 minutes) was washed with borate buffer solution (2 mL, 50 mM, pH7.1). Subsequently, the latex was suspended in borate buffer solution (2 mL, 50 mM, pH7.3) containing 0.5 w/v % BSA, and used it as an anti-human PSA antibody-sensitized latex solution 1).

In addition, by the same way as describe above, borate buffer solution (1 mL, 50 mM, pH7.1) containing 1.4 mg of anti-human PSA monoclonal antibody (Clone No. PSA14; produced by Wako Pure Chemical Industries Ltd.) was mixed with borate buffer solution (1 mL, 50 mM, pH 7.1) in which polystyrene latex with 0.15 μm in particle size (produced by Sekisui Chemical Co., Ltd.) was suspended so as to provide 2 w/v %, and used it as an anti-human PSA antibody-sensitized latex solution 2).

(2) Sample

Phosphate buffer solution (10 mM phosphate buffer solution containing 1 w/v % BSA and 0.85% NaCl) was used as a reagent blanktest sample. As the sample, PSA Calibrator Set (produced by Wako Pure Chemical Industries Ltd.; which includes those with PSA concentration, 5.0 ng/mL, 10.0 ng/mL, 39.8 ng/mL, 69.3 ng/mL, and 98.6 ng/mL, respectively) was used.

(3) Reagent

First Reagent

HEPES-NaOH buffer solutions (0.1 M, pH 7.0), which contain 0.75 w/v % of polymer 1, polymer 2 or polymer 3 synthesized in Synthetic Example 1 as an agglutination enhancer, and include 0.1% BSA and 1% NaCl, were prepared, and thus three kinds of first reagents were prepared.

Second Reagent

Each 2 mL of the anti-human PSA antibody-sensitized latex 1) and the anti-human PSA antibody-sensitized latex 2), which were prepared in the above-described (1), were suspended and mixed with borate buffer solution (16 mL, 50 mM, pH7.5) containing 0.5 w/v % of BSA, and used as a second reagent.

(4) Measurement Method

Using BM-8 Autoanalyzer (manufactured by JEOL Ltd.), the PSA concentration in a sample was measured using the above-described sample, above-described first reagent and above-described second reagent under the following condition:

Sample: 18.0 μL (diluted double with saline);
First reagent: 90 μL;
Second reagent: 30 μL;
Measurement method: 2 point-end method (37 to 65);
Dominant wavelength: 694 nm.

Comparative Example 3: Measurement of PSA by Latex Immunoagglutination Measurement Method Using Conventional Immunoagglutination Enhancer The PSA was measured by the same method as described in Example 3 except for using HEPES-NaOH buffer solution (0.1 M, pH 8.0) which contains 0.4 w/v % of polyethylene glycol 6,000 (PEG 6,000, produced by Wako Pure Chemical Industries Ltd.) or MPC polymer (produced by NOF Corporation) instead of polymer 1 to 3 of Example 3 as an agglutination enhancer, and includes 0.1% BSA and 1% NaCl.

The results were shown in Table 2 in conjunction with the results of Example 3.

TABLE 3

|  | Example 2 | | | Comparative Example 2 | |
|---|---|---|---|---|---|
|  | Agglutination enhancer | | | | |
|  | Polymer 1 | Polymer 2 | Polymer 3 MW | PEG | MPC |
| PSA concentration | 64,340 | 121,752 | 2,644,000 | 6,000 | 245,000 |
| 0 ng/mL (Blank) | −15 | −19 | −12 | −37 | −17 |
| 5 ng/mL | 218 | 252 | 269 | 153 | 178 |
| 10 ng/mL | 453 | 539 | 580 | 257 | 366 |
| 39.8 ng/mL | 2034 | 2720 | 3141 | 989 | 1529 |
| 69.3 ng/mL | 3566 | 4772 | 5464 | 1716 | 2615 |
| 98.6 ng/mL | 4786 | 6271 | 7028 | 2224 | 3735 |

From the results shown in Table 3, it turned out that, in the PSA measurement system, all of polymer 1, 2, and 3 showed higher agglutination enhancing effect than PEG 6,000 and MPC of Comparative Example 3. In addition, it turned out that, as is the case with CRP measurement system and Fer measurement system, the polymer with higher molecular weight showed the more excellent effect.

Example 4: Measurement of CRP by Latex Immunoagglutination Measurement Method Using Various Types of Polymers as an Immunoagglutination Enhancer The CRP was measured by the same method as described in Example 1 except for using 0.1 M Tris buffer solution (pH 8.0) which contains 0.4 w/v % of polymer 4 to 6 as an agglutination enhancer instead of polymer 1 to 3, and includes 0.1% BSA and 1% NaCl as a first reagent, and. The results were shown in Table 4.

TABLE 4

|  | Agglutination enhancer | | |
|---|---|---|---|
| CRP concentration | Polymer 4 | Polymer 5 | Polymer 6 |
| 0 mg/mL (Blank) | 48 | 51 | 48 |
| 0.2 mg/dL | 434 | 399 | 386 |
| 1.0 mg/dL | 1451 | 1370 | 1314 |
| 4.0 mg/dL | 2602 | 2493 | 2409 |
| 18.0 mg/dL | 5902 | 5645 | 5421 |
| 35.0 mg/dL | 7618 | 7280 | 7081 |

From the results shown in Table 4, it turned out that, in the CRP measurement system, all of polymer 4, 5, and 6 showed high agglutination enhancing effect as is the case with polymer 1, 2, and 3. In addition, it turned out that the polymers showed higher agglutination enhancing effect than PEG 6,000 and MPC which were the conventional agglutination enhancers.

Example 5: Measurement of Fer by Latex Immunoagglutination Measurement Method Using Various Types of Polymers as an Immunoagglutination Enhancer The Fer was measured by the same method as described in Example 2 except for using 0.1 M Tris buffer solution (pH 8.0) which contains 0.4 w/v % polymer 4 to 6 as an agglutination enhancer instead of polymer 1 to 3 and includes 0.1% BSA and 1% NaCl as a first reagent. The results were shown in Table 5.

TABLE 5

|  | Agglutination enhancer | | |
|---|---|---|---|
| Fer concentration | Polymer 4 | Polymer 5 | Polymer 6 |
| 0 ng/mL (Blank) | −27 | −33 | −31 |
| 30 ng/mL | 120 | 99 | 92 |
| 100 ng/mL | 463 | 438 | 407 |
| 200 ng/mL | 992 | 951 | 890 |
| 500 ng/mL | 2500 | 2389 | 2263 |
| 1000 ng/mL | 3768 | 3678 | 3566 |

From the results shown in Table 5, it turned out that, also in the Fer measurement system, all of polymer 4, 5, and 6 showed high agglutination enhancing effect as is the case with polymer 1, 2, and 3. In addition, it turned out that the polymers showed higher agglutination enhancing effect than PEG 6,000 and MPC which were the conventional agglutination enhancers.

Example 6: Measurement of PSA by Latex Immunoagglutination Measurement Method Using Various Types of Polymers as an Immunoagglutination Enhancer The PSA was measured by the same method as described in Example 3 except for using 0.1 M HEPES-NaOH buffer solution (pH 7.0) which contains 0.4 w/v % polymer 4 to 6 instead of polymer 1 to 3 as an agglutination enhancer and includes 0.1% BSA and 1% NaCl as a first reagent. The results were shown in Table 6.

TABLE 6

|  | Agglutination enhancer | | |
| --- | --- | --- | --- |
| PSA concentration | Polymer 4 | Polymer 5 | Polymer 6 |
| 0 ng/mL (Blank) | −13 | −15 | −17 |
| 5 ng/mL | 210 | 238 | 222 |
| 10 ng/mL | 440 | 485 | 446 |
| 39.8 ng/mL | 2027 | 2281 | 2063 |
| 69.3 ng/mL | 3571 | 3986 | 3642 |
| 98.6 ng/mL | 4877 | 5663 | 4905 |

From the results shown in Table 6, it turned out that, in the PSA measurement system, all of polymer 4, 5, and 6 showed high agglutination enhancing effect as is the case with polymer 1, 2, and 3. In addition, it turned out that the polymers showed higher agglutination enhancing effect than that PEG 6,000 and MPC which were the conventional agglutination enhancers.

Example 7: Measurement of CRP by Latex Immunoagglutination Measurement Method Using a Copolymer as an Immunoagglutination Enhancer The CRP was measured by the same method as described in Example 1 except for using 0.1 M Tris buffer solution (pH 8.0) which contains 0.4 w/v % of copolymer 1 or 2 as an agglutination enhancer instead of polymer 1 to 3 and includes 0.1% BSA and 1% NaCl as a first reagent. The results were shown in Table 7.

TABLE 7

|  | Polymer | |
| --- | --- | --- |
|  | Copolymer 1 | Copolymer 2 |
|  | Molecular weight | |
|  | 658,206 | 957,680 |
|  | Monomer 1 content | |
| CRP concentration | 5% | 40% |
| 0 mg/dL (Blank) | 49 | 47 |
| 0.2 mg/dL | 655 | 463 |
| 1.0 mg/dL | 1802 | 1510 |
| 4.0 mg/dL | 2914 | 2688 |
| 18.0 mg/dL | 6565 | 6183 |
| 35.0 mg/dL | 8202 | 7927 |

From the results shown in Table 7, it turned out that, in the CRP measurement system, both copolymer 1 and 2 showed high agglutination enhancing effect as is the case with polymer 1 to 6. In addition, it also turned out that the copolymers showed higher agglutination enhancing effect than PEG 6,000 and MPC which were the conventional agglutination enhancers.

Example 8: Measurement of Fer by Latex Immunoagglutination Measurement Method Using a Copolymer as an Immunoagglutination Enhancer The Fer was measured by the same method as described in Example 2 except for using 0.1 M HEPES-NaOH buffer solution (pH 7.0) which contains 0.4 w/v % copolymer 1 or 2 as an agglutination enhancer instead of polymer 1 to 3 and includes 0.1% BSA and 1% NaCl as a first reagent. The results were shown in Table 8.

TABLE 8

|  | Polymer | |
| --- | --- | --- |
|  | Copolymer 1 | Copolymer 2 |
|  | Molecular weight | |
|  | 658,206 | 957,680 |
|  | Monomer C content | |
| Fer concentration | 5% | 40% |
| 0 ng/mL (Blank) | −33 | −41 |
| 30 ng/mL | 129 | 107 |
| 100 ng/mL | 496 | 453 |
| 200 ng/mL | 1133 | 987 |
| 500 ng/mL | 2828 | 2503 |
| 1000 ng/mL | 3876 | 3679 |

From the results shown in Table 8, it turned out that, in the Fer measurement system, both copolymer 1 and 2 showed high agglutination enhancing effect as is the case with polymer 1 to 6. In addition, it also turned out that the copolymers showed higher agglutination enhancing effect than PEG 6,000 and MPC which were the conventional agglutination enhancers.

Example 9: Measurement of PSA by Latex Immunoagglutination Measurement Method Using a Copolymer as an Immunoagglutination Enhancer The PSA was measured by the same method as described in Example 3 except for using 0.1 M HEPES-NaOH buffer solution (pH 7.0) which contains 0.75 w/v % copolymer 1 or 2 as an agglutination enhancer instead of polymer 1 to 3 and includes 0.1% BSA and 1% NaCl, and, as a first reagent. The results were shown in Table 9.

TABLE 9

|  | Polymer | |
| --- | --- | --- |
|  | Copolymer 1 | Copolymer 2 |
|  | Molecular weight | |
|  | 658,206 | 957,680 |
|  | Monomer C content | |
| PSA concentration | 5% | 40% |
| 0 mg/dL (Blank) | −16 | −13 |
| 5 ng/mL | 282 | 246 |
| 10 ng/mL | 598 | 529 |
| 39.8 ng/mL | 3212 | 2634 |
| 69.3 ng/mL | 5453 | 4583 |
| 98.6 ng/mL | 6992 | 5975 |

From the results shown in Table 9, it turned out that, in the PSA measurement system, both copolymer 1 and 2 showed high agglutination enhancing effect as is the case with polymer 1 to 6. In addition, it also turned out that the copolymers showed higher agglutination enhancing effect than PEG 6,000 and MPC which were the conventional agglutination enhancers.

Example 10: Measurement of CK-MB by Latex Immunoagglutination Measurement Method Using a Copolymer as an Immunoagglutination Enhancer (1) Preparation of Anti-Human CK-MB Antibody-Sensitized (Immobilized) Latex Reagent Borate buffer solution (1 mL, 50 mM, pH 7.5) containing 0.8 mg/mL of anti-human CK-MB monoclonal antibody (Clone MAK <CK-MB> M-7.4.5-IgG; produced by Roche Diagnostics GmbH) was mixed with borate buffer solution (1 mL, 50 mM, pH 7.5) in which polystyrene latex with 0.4 μm in particle size (produced by Fujikura Kasei Co., Ltd.) was suspended so as to contain 2 w/v %, and reacted at 25° C. for 2 hours. Then, whole quantity of the latex separated from the aforementioned suspension by centrifugal separation (45,000×g, 30 minutes) was washed with borate buffer solution (2 mL, 50 mM, pH7.5). Subsequently, the latex was suspended in borate buffer solution (2 mL, 50 mM, pH7.5) containing 0.5 w/v % BSA, and used it as an anti-human CK-MB antibody-sensitized latex solution 1).

In addition, by the same way as describe above, borate buffer solution (1 mL, 50 mM, pH7.5) containing 0.8 mg of anti-human CK-MB monoclonal antibody (Clone MAK <CK-MB> M-6.12.47-IgG; produced by Roche Diagnostics GmbH) was mixed with borate buffer solution (1 mL, 50 mM, pH 7.5) in which polystyrene latex with 0.4 μm in particle size (produced by Fujikuraanalyte Kasei Co., Ltd.) was suspended so as to contain 2 w/v %, and used it as an anti-human CK-MB antibody-sensitized latex solution 2).

(2) Sample

Saline (0.85% NaCl) was used for a reagent blank test sample. The sample was prepared by diluting CK-MB antigen (CK-MB of human origin, produced by Cliniqa Diagnostics Inc.) with phosphate buffer solution (containing 10 mM phosphate, 1 w/v % BSA and 0.85% NaCl) so that its concentration is 5.2 ng/mL, 19.0 ng/mL, 47.9 ng/mL, 98.7 ng/mL, and 204.3 ng/mL, respectively, and used them as samples.

(3) Reagent

First Reagent

HEPES-NaOH solutions (0.1 M, pH 7.0), which contains 0.75 w/v % of polymer 1, copolymer 1, or copolymer 2 and includes 0.1% BSA and 1% NaCl, were prepared, and thus three kinds of first reagents were prepared.

Second Reagent

The anti-human CK-MB antibody-sensitized latex solution 1) and 2) (2 mL each) prepared in the above-described (1) were suspended in 50 mM borate buffer solution (pH7.5) containing 0.5 w/v % BSA and mixed, and used it as a second reagent.

(4) Measurement Method

Using BM-8 Autoanalyzer (produced by JEOL Ltd.), the CK-MB concentration in a sample was measured using the above-described sample, above-described first reagent and above-described second reagent under the following condition:

Sample: 12.0 μL (diluted double with saline);
First reagent: 90 μL;
Second reagent: 30 μL;
Measurement method: 2 point-end method (35 to 59);
Dominant wavelength: 596 nm.

The obtained results were shown in Table 10.

Comparative Example 4: Measurement of CK-MB by Latex Immunoagglutination Measurement Method Using Conventional Immunoagglutination Enhancer The CK-MB was measured by the same method as described in Example 10 except for using 0.1 M HEPES-NaOH buffer solution (pH 7.0) which contains 0.75 w/v % polyethylene glycol 6,000 (PEG 6,000, produced by Wako Pure Chemical Industries Ltd.) or MPC polymer (produced by NOF Corporation) as an agglutination enhancer instead of polymer 1, copolymer 1 and copolymer 2 and includes 0.1% BSA and 1% NaCl as a first reagent. The results were shown in Table 10 in conjunction with the results of Example 10.

TABLE 10

|  | Example 10 | | | Comparative Example 4 | |
| --- | --- | --- | --- | --- | --- |
|  | Agglutination enhancer | | | | |
|  | Polymer 2 | Copolymer 1 | Copolymer 2 | PEG | MPC |
|  | Molecular weight | | | | |
|  | 121,752 | 658,206 | 957,680 | 6000 | 245,000 |
| CK-MB | Monomer C content | | | | |
| concentration | 0% | 5% | 40% | | |
| 0 ng/mL (Blank) | −102 | −65 | −31 | −139 | −129 |
| 5.2 ng/mL | 83 | 90 | 93 | 19 | 24 |
| 19.0 ng/mL | 481 | 599 | 810 | 85 | 197 |
| 47.9 ng/mL | 1439 | 1789 | 2232 | 257 | 624 |
| 98.7 ng/mL | 2547 | 2942 | 3198 | 534 | 1220 |
| 204.3 ng/mL | 3335 | 3502 | 3590 | 1134 | 2232 |

From the results shown in Table 10, it turned out that, in the CK-MB measurement system, addition of any of polymer 2, copolymer 1 and copolymer 2 showed higher agglutination enhancing effect than PEG 6,000 and MPC of Comparative Example 4. Moreover, it turned out that the copolymer 1 and copolymer 2 which were copolymers showed higher agglutination enhancing effect than the polymer 2 which was a homopolymer.

Example 11: Measurement of CRP by Latex Immunoagglutination Measurement Method in Different Content of Immunoagglutination Enhancer The CRP was measured by the same method as described in Example 1 except for using 0.1 M Tris buffer solution (pH 8.0) which contains 0.24 w/v %, 0.32 w/v %, 0.56 w/v %, or 0.72 w/v % of polymer 1 and includes 0.1% BSA and 1% NaCl as a first reagent. The results were shown in Table 11.

TABLE 11

|  | Polymer 1 added | | | |
| --- | --- | --- | --- | --- |
| CRP concentration | 0.24% | 0.32% | 0.56% | 0.72% |
| 0 mg/dL | 64 | 68 | 54 | 54 |
| 0.2 mg/dL | 238 | 298 | 526 | 795 |
| 1.0 mg/dL | 1035 | 1316 | 2048 | 2703 |
| 4.0 mg/dL | 2265 | 2630 | 3477 | 4208 |
| 18.0 mg/dL | 4923 | 5691 | 7441 | 8568 |
| 35.0 mg/dL | 6513 | 7556 | 8968 | 9408 |

As is clear from the results of Table 11, it turned out that, in the CRP measurement system, the more the additive amount of polymer 1 was, the agglutination enhancing effect became higher.

Example 12: Measurement of Fer by Latex Immunoagglutination Measurement Method in Different Content of Immunoagglutination Enhancer The Fer was measured by the same method as described in Example 2 except for using 0.1 M HEPES-NaOH buffer solution (pH 7.0) which contains 0.25 w/v %, 0.31 w/v %, 0.49 w/v %, or 0.61 w/v % of polymer 1 and includes 0.1% BSA and 1% NaCl as a first reagent. The results were shown in Table 12.

TABLE 12

| Fer concentration | Polymer 1 added | | | |
|---|---|---|---|---|
| | 0.25% | 0.31% | 0.49% | 0.61% |
| 0 ng/mL | −27 | −24 | −44 | −40 |
| 30 ng/mL | 79 | 87 | 128 | 156 |
| 100 ng/mL | 276 | 321 | 457 | 564 |
| 200 ng/mL | 579 | 659 | 971 | 1252 |
| 500 ng/mL | 1501 | 1720 | 2541 | 3319 |
| 1000 ng/mL | 2797 | 3143 | 4023 | 4500 |

As is clear from the results of Table 12, it turned out that, in the Fer measurement system, the more the additive amount of polymer 1 was, the agglutination enhancing effect became higher.

Example 13: Measurement of PSA by Latex Immunoagglutination Measurement Method in Different Content of Immunoagglutination Enhancer The PSA was measured by the same method as described in Example 3 except for using 0.1 M HEPES-NaOH buffer solution (pH 7.0) which contains 0.60 w/v %, 0.90 w/v %, 1.35 w/v %, or 1.50 w/v % of polymer 1 and includes 0.1% BSA and 1% NaCl as a first reagent. The results were shown in Table 13.

TABLE 13

| PSA concentration | Polymer 1 added | | | |
|---|---|---|---|---|
| | 0.60% | 0.90% | 1.35% | 1.50% |
| 0 ng/mL | −17 | −17 | −12 | −3 |
| 4.9 ng/mL | 189 | 236 | 341 | 389 |
| 10.0 ng/mL | 391 | 520 | 781 | 1024 |
| 40.1 ng/mL | 1741 | 2531 | 4654 | 5847 |
| 69.8 ng/mL | 3054 | 4502 | 7239 | 8044 |
| 99.2 ng/mL | 4208 | 5959 | 8524 | 9247 |

As is clear from the results of Table 13, it turned out that, in the PSA measurement system, the more the additive amount of polymer 1 was, the agglutination enhancing effect became higher.

The invention claimed is:

1. A method of measuring agglutination, which comprises bringing an antibody or an antigen against an analyte into contact with the analyte, to cause an antigen-antibody reaction, in the presence of a polymer that is either
(a) a homopolymer consisting of a monomer unit of formula [1]:

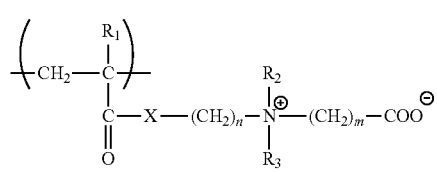

[1]

wherein $R_1$ is a hydrogen atom or a methyl group; $R_2$ and $R_3$ are a methyl group, X is —NH— or an oxygen atom; n is an integer of 2 to 4; and m is an integer of 1
or
(b) a copolymer consisting of
(i) a monomer unit of formula [1]:

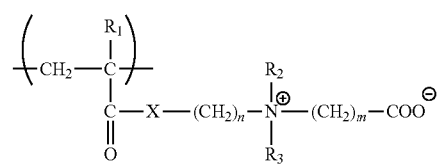

[1]

wherein $R_1$ is a hydrogen atom or a methyl group; $R_2$ and $R_3$ are a methyl group, X is —NH— or an oxygen atom; n is an integer of 2 to 4; and m is an integer of 1, and
(ii) a monomer unit of formula [2]:

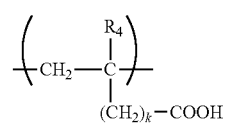

[2]

wherein $R_4$ is a hydrogen atom or a methyl group, and k is an integer of 4 to 8, to generate agglutination and form particles from the antigen-antibody reaction, and measuring the degree of agglutination of the particles based on a change of scattered light or transmitted light.

2. The method according to claim 1, wherein the analyte is C-reactive protein (CRP), serum ferritin (Fer), prostate specific antigen (PSA), or creatine kinase-MB (CK-MB).

3. The method according to claim 1, wherein the content of the monomer unit of formula [1] in the copolymer is 50% by mole or more and less than 100% by mole.

4. The method according to claim 1, wherein the polymer has a weight-average molecular weight of 50,000 to 3,000,000 g/mol.

5. A method of measuring agglutination, which comprises bringing an antibody or an antigen against an analyte into contact with the analyte, to cause an antigen-antibody reaction, in the presence of a polymer that is either
(a) a homopolymer consisting of a monomer unit that is

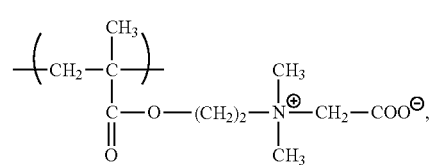

(1-1-1)

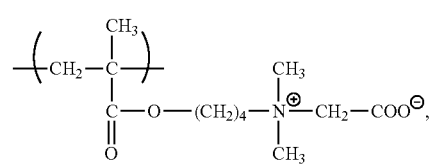

(1-1-2)

-continued
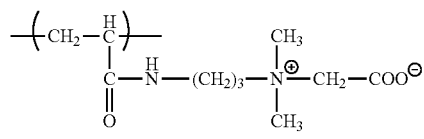 [1-3-1] or
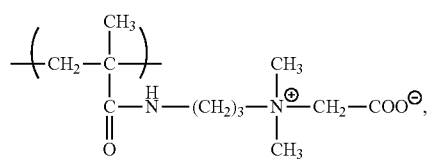 [1-4-1]
or
(b) a copolymer consisting of
(i) a monomer unit that is
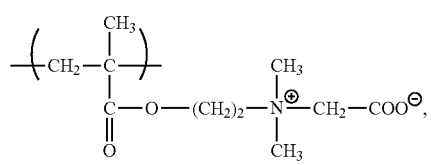 [1-1-1]
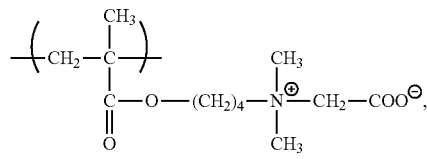 [1-1-2]
-continued
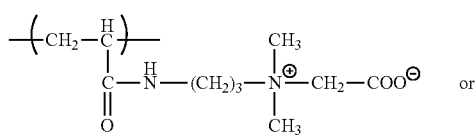 [1-3-1] or
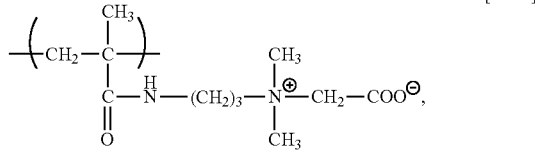 [1-4-1]
and
(ii) a monomer unit of formula [2-1-1]:
 [2-1-1]
to generate agglutination and form particles from the antigen-antibody reaction, and
measuring the degree of agglutination of the particles based on a change of scattered light or transmitted light.
\* \* \* \* \*